United States Patent
Shkarlet

(10) Patent No.: US 8,214,168 B2
(45) Date of Patent: Jul. 3, 2012

(54) NONINVASIVE TESTING OF A MATERIAL INTERMEDIATE SPACED WALLS

(75) Inventor: Yuri Shkarlet, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 1199 days.

(21) Appl. No.: 10/935,052

(22) Filed: Sep. 7, 2004

(65) Prior Publication Data

US 2006/0052963 A1   Mar. 9, 2006

(51) Int. Cl.
*G01D 3/00* (2006.01)
*G06F 19/00* (2011.01)
(52) U.S. Cl. ......... 702/108; 702/100; 702/104; 702/106
(58) Field of Classification Search .................. 702/122, 702/13–116, 183; 73/24.01, 861.27, 861.29, 73/61.49
See application file for complete search history.

(56) References Cited

U.S. PATENT DOCUMENTS

| | | |
|---|---|---|
| 3,939,707 A | 2/1976 | Kossoff |
| 3,940,731 A | 2/1976 | Cooper et al. |
| 4,145,925 A | 3/1979 | Stasz et al. |
| 4,227,407 A | 10/1980 | Drost |
| 4,257,278 A | 3/1981 | Papadofrangakis et al. |
| 4,397,191 A | 8/1983 | Forden |
| 4,660,607 A | 4/1987 | Griffith et al. |
| 5,020,374 A | 6/1991 | Petroff et al. |
| 5,095,514 A | 3/1992 | Curtis |
| 5,453,576 A | 9/1995 | Krivitski |
| 5,633,809 A | 5/1997 | Wissenbach et al. |
| 5,969,263 A | 10/1999 | Ligneul et al. |
| 5,986,553 A | 11/1999 | Young |
| 6,003,385 A | 12/1999 | De Vanssay et al. |
| 6,098,466 A | 8/2000 | Shkarlet |
| 6,158,288 A | 12/2000 | Smith |
| 6,216,544 B1 | 4/2001 | Adachi et al. |
| 6,293,156 B1 * | 9/2001 | Shen et al. ............... 73/861.26 |
| 6,295,874 B1 | 10/2001 | Strutt et al. |
| 6,318,179 B1 | 11/2001 | Hamilton et al. |
| 6,408,699 B1 | 6/2002 | Moss et al. |
| 6,544,181 B1 | 4/2003 | Buck et al. |

(Continued)

FOREIGN PATENT DOCUMENTS

AT          380 339 B     9/1985

(Continued)

OTHER PUBLICATIONS

Apr. 26, 2010 Office Action in corresponding Japanese Patent Application No. 2007-530404, along with a summarized English translation (5 pages).

(Continued)

*Primary Examiner* — Phuong Huynh
(74) *Attorney, Agent, or Firm* — Brian B. Shaw, Esq.; Harter Secrest & Emery LLP

(57) ABSTRACT

A sensor probe provides a pair of unique signal paths through a test material, wherein one configuration of the probe provides identical external portions of the signal paths such that a selected parameter of a measuring signal passing along at least two of the unique signal paths is measured. From these measurements, a method is provided for calculating at least one parameter of the test material, wherein the parameter can include an intrinsic parameter as well as a condition of state.

39 Claims, 7 Drawing Sheets

U.S. PATENT DOCUMENTS

| | | | |
|---|---|---|---|
| 6,550,345 B1 * | 4/2003 | Letton | 73/861.27 |
| 6,740,036 B1 | 5/2004 | Lee et al. | |
| 7,013,240 B2 * | 3/2006 | Malik et al. | 702/183 |
| 2002/0078737 A1 * | 6/2002 | Zanker | 73/61.79 |
| 2004/0035190 A1 * | 2/2004 | Sinha | 73/61.49 |
| 2004/0129088 A1 * | 7/2004 | Moscaritolo et al. | 73/861.25 |
| 2004/0254469 A1 * | 12/2004 | Shkarlet et al. | 600/459 |

FOREIGN PATENT DOCUMENTS

| | | | |
|---|---|---|---|
| JP | 02-112757 | * | 4/1990 |
| JP | 04-194663 | * | 7/1992 |
| JP | 10-318920 | | 12/1998 |
| JP | H11-248622 | | 9/1999 |
| JP | 2001-289780 | | 10/2001 |
| JP | 2003-57194 | | 2/2003 |
| WO | 2004/020112 | | 3/2004 |

OTHER PUBLICATIONS

Oct. 5, 2010 Office Action in corresponding Japanese Patent Application No. 2007-530404, along with a summarized English translation (6 pages).

Japanese Office Action dated Apr. 19, 2011 (A Summarized English Translation) in corresponding JP Application No. 2007-530404, filed Sep. 1, 2005 (3 pages).

* cited by examiner

NONINVASIVE TESTING OF A MATERIAL INTERMEDIATE SPACED WALLS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present invention relates to determining a parameter of a test material and, more particularly, to passing a pair of measuring signals along a pair of different length signal paths within the test material to obtain a pair of measurements from which at least one parameter of the test material is determined.

2. Description of Related Art

The measurement of test materials and particularly those test materials in a liquid or fluid state has been accomplished by a number of mechanisms.

For example, U.S. Pat. No. 3,939,707 discloses a cross-sectional visualization of the portion of the vessel to be examined, the portion lying in a plane of the visualization.

U.S. Pat. No. 4,257,278 discloses a quantitative volume blood flow measurement by an ultrasound imaging system having a Doppler modality.

U.S. Pat. No. 5,095,514 discloses a fiber optic sensor having a body of a matrix material that includes an embedded length of optical fiber, the body being arranged such that when exposed to an external disturbance, a transduction effect will cause corresponding mechanical stresses and strains to be developed internally and applied to the fiber. The resulting stresses and strains in the fiber cause a modification of the light transmission behavior that can be detected in the passage of light through the fiber optic length.

U.S. Pat. No. 6,216,544 discloses an ultrasonic flowmeter for measuring a flow of a fluid by use of an ultrasonic wave. The flowmeter includes a flow measurement section and a pair of ultrasonic oscillators constructed so that the influence of the phase difference between the direct wave and the reflected wave on the measurement results is reduced.

U.S. Pat. No. 6,318,179 discloses an ultrasound system for imaging a subject, having a first matter and a second matter, with the first matter moving with respect to the second matter in a first direction. In such an environment, the preferred embodiment enables determination of the quantitative movement of the first matter with respect to the second matter by transmitting into the subject a beam of ultrasound waves having a predetermined size and defining a plurality of beam positions and a beam axis moved in one or more scan directions having one or more scan direction components parallel to the first direction. First reflected ultrasound waves are received from the first matter and second ultrasound waves are received from the second matter in response to the beam positions in the one or more scan directions.

However, the need remains for increasing the accuracy of the determined parameters of the test material. The need further exists for reducing or eliminating the influence of a probe, a container or conduit parameters as well as transient variables such as temperature or pressure. The need also exists for a system that can provide simultaneous measurement of several parameters of the test material, wherein the measured results form components of a matrix to allow additional increase in accuracy and reliability through data processing.

BRIEF SUMMARY OF THE INVENTION

The present invention provides an apparatus and method for measuring a test material to provide increased accuracy of calculated test material parameters while reducing influence of a probe, a container or conduit parameters as well as transient variations. The present invention provides an improvement in the simultaneous and accurate measurement of parameters of the test material, with reduced impact of transients. Generally, parameters of the test material can be determined independent of wall (or shell or conduit) properties and environmental influences, by employing unique predetermined signal paths through the test material. The unique signal paths can be provided by subjecting the test material to a known reshaping or deformation, knowing the difference between the shapings or formations, or employing static linear signal paths with a known or measured length difference within the test material. In one configuration, the reshaping provides the known difference between the linear signal paths extending through the test material.

Representative test materials that can be reconfigured include a liquid flowing through flexible tubing such as polymer tubing, human or animal tissue. Contained liquids as well as canned materials, and particularly those that are able to withstand deformation, can be measured by the present invention.

Generally, the material to be tested is placed within a measuring zone of the sensor probe, wherein at least two unique signal paths are provided, such that the surrounding or external portions (outside the test material) of the signal paths are identical. The signal paths are unique in that the paths differ only by a preset, known or measured straight-line distance through the test material.

The present invention provides a pair of signal paths through the test material, wherein the signal paths have identical (or known) portions external to the test material and differing straight line lengths within the test material, with the difference in internal lengths being known (or measured). Thus, the internal length of one signal path is shorter than the internal length of the remaining signal path.

At least one pair of measuring signals is transmitted along the signal paths—a first measuring signal along the first signal path and a second measuring signal along the second signal path. The transmission of the pair of measuring signals can be simultaneous or serial.

A parameter of each measuring signal or of the pair of signals is measured, sensed or determined. Preferably, the same signal parameter is measured for each signal of measuring signals pair.

From one pair of measurements, one intrinsic parameter of the test material can be determined.

Pairs or sets of measurements are taken from a pair of measuring signals passing along the signal paths—one measuring signal passing along the first signal path and the other measuring signal passing along the remaining signal path. The measurements are processed to provide information on the test material and/or the state of the test material, and/or a temporary or a transient change, including changes such as an introduced bolus, which are independent of the influence of the conduit (shell), as well as a sensor probe, the conduit (container) walls and temperature effects of each of the components. The measuring signals can be selected to correspond to local variations in the test material or conditions such as temperature deviations, salinity, pressure, color, transparency or conductivity. However, multiple parameters of a given measuring signal pair can be measured so that two or more intrinsic parameters of the test material can be determined.

In one configuration, the present method provides for measuring a test material between at least two spaced walls by passing the measuring signal along a first and a second signal path, each signal path passing through both spaced walls and having (a) a different straight-line length within the test material and (b) one of an equal or known path length external to the test material, and measuring at least one signal parameter of the measuring signal path along the first signal path and the second signal path. The signal parameters that can be measured include at least one of a phase, amplitude, frequency, attenuation coefficient or time of flight of the measuring signal. At least one parameter of the test material corresponding to the first and second measurement of the signal parameter is then determined.

In a further configuration, a sensor probe is provided for measuring a test material located between spaced walls. The sensor probe includes a first sensor assembly having a first signal path with a first external component including both walls and a first straight length internal component passing through the test material, and a second sensor assembly having a different second signal path, the second signal path including a second external component including both walls and a second straight-line internal component passing through the test material, the first external component being equal to the second external component and the first internal component being different than the second internal component. A controller is connected to the first sensor assembly and the second sensor assembly to determine a characteristic or state of the test material in response to a parameter of a measuring signal passing along the first signal path and a second signal path.

Yet another configuration provides a sensor probe having a first sensor assembly having a signal path extending between a pair of sensors, the sensors movable a known distance between a first position and a spaced second position. A measuring signal is passed along the signal path with the sensors in the first position, and a parameter of the measuring signal is measured. The sensor probe then disposes the transducers in the second position, and the parameter of a measuring signal is again measured. From these two measurements and the known difference between the first position and the second position, a parameter of the test material is calculated.

BRIEF DESCRIPTION OF THE SEVERAL VIEWS OF THE DRAWING(S)

DETAILED DESCRIPTION OF THE INVENTION

Figure 1:
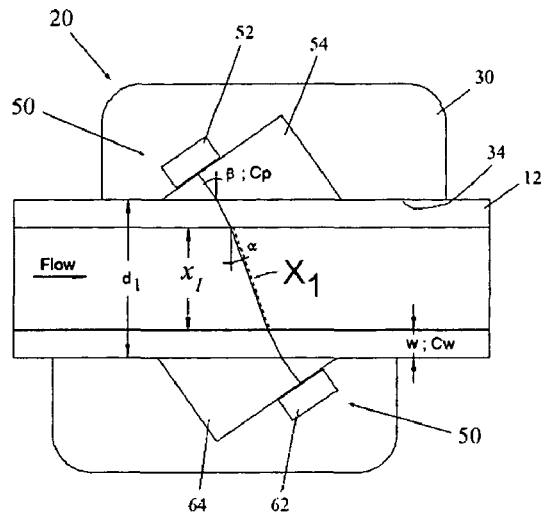
FIG. 1 is a cross-sectional view of a dynamic sensor probe in a first configuration.
Figure 2:
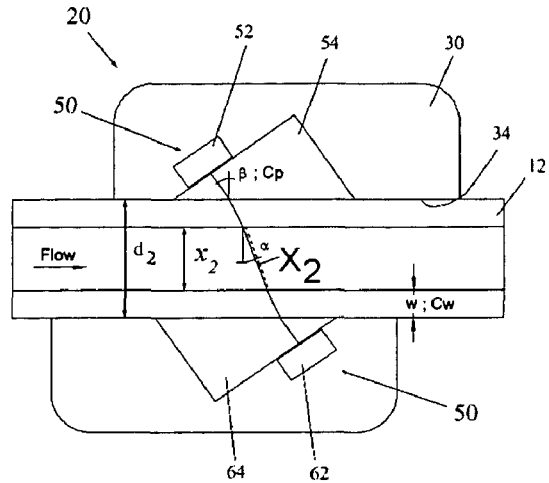
FIG. 2 is a cross-sectional view of the sensor probe of FIG. 1 in a second configuration.

Referring to FIGS. 1 and 2, a dynamic sensor probe 20 is shown for measuring a test material, such as a fluid flow through a conduit 12. The dynamic sensor probe 20 can be a clamp-on sensor for cooperatively engaging a deformable conduit 12, wherein the test material flows or is disposed within the conduit.

Generally, in a first configuration, the sensor probe 20 locates the test material within a measuring zone, such that at least two unique linear signal paths are provided through the test material. The two signal paths differ only in the predetermined straight-line distance through the test material, while an external element of the signal paths (and sensors) are sufficiently or essentially identical. The external elements of each of the signal paths are preferably selected to have at least substantially the same influence on a measuring signal. The differing straight-line distance through the test material can be accomplished either dynamically or statically. That is, the sensor probe 20 can be reconfigured, between sets of measurements, to define the unique signal paths (dynamic) or the sensor probe can retain the test material so as to define the two signal paths or measuring volumes (static). That is, the signal paths are different in the amount of test material in each signal path.

Preferably, the dynamic sensor probe 20 is configurable between two preset positions with a known difference in the volume or deformation of the test material. A first measurement is taken of a signal parameter with the sensor probe in the first position, and a second measurement is taken of the signal parameter with the sensor probe in the second position. A known change of volume in the measuring zone occurs between the first measurements and the second measurements, while the surrounding portions of the signal path and sensors remain constant.

The dynamic sensor probe 20 includes a housing 30 and a sensor assembly 50. The housing 30 can include a moveable lid and defines a channel 34 for defining signal paths of different length within the conduit 12. The sensor assembly 50 includes an upstream transducer 52, an upstream prism 54, a downstream transducer 62 and a downstream prism 64.

The term transducer encompasses any substance or device, such as a piezoelectric crystal, microphone, or photoelectric cell, that converts an input energy of one form into an output energy of another form. Such conversions include, but are not limited to electrical-mechanical; optical-mechanical; optical-chemical as well as electrical-optical. A sensor includes a transducer responding to a physical stimulus which generates/receives the signal before/after interaction with the test material. For example, the sensor can include a piezoelectric element with matching acoustic layers. The sensor probe 20 is thus an arrangement of at least one sensor for a particular purpose.

Although the present configuration of the sensor probe 20 is set forth as employing ultrasound sensors with ultrasound measuring signals and transducers, it is understood that any of a variety of sensors which can detect a measuring signal passing along the signal path can be employed. The sensors and measuring signal can include but are not limited to optical, electrical, physical, acoustical, or electromagnetic, or any combination thereof. Similarly, the signal parameter that is measured (or sensed) by the sensor can be any of a variety of signal parameters, such as but not limited to time delay, time of flight, intensity, attenuation, frequency, amplitude, phase as well as time and/or space characteristics including, but not limited to electrical resistivity, impedance, admittance or conductivity, optical transparency or absorption as a function of optical wavelength, voltage and/or current.

A signal path is defined from the upstream (first) transducer 52 to the downstream (second) transducer 62, the signal path including a portion extending through the upstream prism 54, a first conduit wall, the test material, a second conduit wall and the downstream prism 64.

The signal path is preferably defined in terms of an internal portion and an external portion. The internal portion of the signal path is that portion ($X_1$, $X_2$) passing through the test material. The external portion of the signal path is all the remaining portion of the signal path and, as seen in FIG. 1, includes the upstream prism 54, the first conduit wall, the second conduit wall, the downstream prism 64 as well as any interconnecting coupling gels, glues or materials, and any portions of the housing 30 through which the measuring signal passes.

Although the term "conduit" is used, it is understood the test material can be located within a channel, groove or other flow path. Further, the term conduit is intended to encompass any type of flow containing structure, independent of the material. Thus, conduit 12 includes any material that retains the test material and through which the measuring signal can pass. Therefore, conduit 12 encompasses rigid and flexible ducts, containers, cans or pipes formed of metal, composites, laminates, or polymers.

Generally, the present invention employs a known difference between linear signal paths through the test material. The known difference can be obtained by a measurement, calibration, or known values of the different signal paths. For example, and without limiting the disclosure, referring to FIG. 1, $d_1$ is a fixed distance between the prisms 54, 64; $\chi_1$ is a distance between the inner walls of the conduit 12; $X_1$ is the linear (straight) line length of the internal portion of the signal path and $\alpha$ is the angle at which the measuring signal [wave] enters the test material.

The length of the straight internal portion $X_1$ of the signal path is determined by:

$$X_1 = \frac{\chi_1}{\cos\alpha}$$

Referring to FIG. 2, the prisms 54, 64 (and associated transducers) have been shifted towards each other by a predetermined (or known or measured) distance $\Delta d$, such that the prisms are separated by distance $d_2$ and the inner walls of the conduit are separated by a corresponding distance $\chi_2$. Assuming no or only insignificant compression of the conduit walls, the external portion of the signal path remains constant. That is, only the length of the signal path X through the test material changes. The change in positions is expressed as:

$$\Delta d = d_1 - d_2 = \chi_1 - \chi_2$$

As the prisms 54, 64 have been moved, the distance $\chi_2$ differs from $\chi_1$, and hence the signal path has changed. Thus, a first unique signal path is provided with the sensor probe 20 in the first position, and a different second unique signal path is formed by the sensor probe in the second position.

The length of the internal straight path $X_2$ is determined by:

$$X_2 = \frac{\chi_2}{\cos\alpha}$$

Alternatively stated:

$$d_2 = d_1 - \Delta d; \chi_2 = \chi_1 - \Delta d; \text{ and } X_2 = X_1 - \frac{\Delta d}{\cos\alpha}$$

Knowing the difference in the internal portions of the signal paths, the measuring signal is considered. The time of flight (TOF) $T_1$ for an acoustic measuring signal passing along the signal path from the upstream transducer 52 to the downstream transducer 62, as shown in FIG. 1, is:

$$T_1 = \sum T_e + \frac{X_1}{(C + V\sin\alpha)} \tag{1}$$

where $\Sigma T_e$ is the total time of flight of the measuring signal along the external portion of the signal path, C is the intrinsic velocity of sound in the test media, and V is the velocity of the test material flow through the conduit 12.

The time of flight ($T_2$) for an acoustic measuring signal passing along the signal path from the downstream transducer 62 to the upstream transducer 52, as shown in FIG. 1, is:

$$T_2 = \sum T_e + \frac{X_1}{(C - V\sin\alpha)} \tag{2}$$

Upon disposing the sensor probe 20 in the second configuration shown in FIG. 2, the second unique signal path is formed and the time of flight ($T_3$) for an acoustic measuring signal passing along the signal path from the upstream transducer 52 to the downstream transducer 62 is:

$$T_3 = \sum T_e + \frac{X_2}{(C + V\sin\alpha)} \tag{3}$$

The time of flight ($T_4$) for an acoustic measuring signal passing along the signal path from the downstream transducer 62 to the upstream transducer 52, as shown in FIG. 2, is:

$$T_4 = \sum T_e + \frac{X_2}{(C - V\sin\alpha)} \quad (4)$$

It is understood that $T_e$ and $\Sigma T_e$ can vary substantially, such as for different types and/or materials of flow containing structure or in response to temperature changes. Further, dependencies such as pressure and time can also exist.

From Snell's law, the following relationship exists:

$$\frac{\sin\beta}{C_p} = \frac{\sin\alpha}{C} \quad (5)$$

where $C_p$ is the velocity of sound in the prism 54, 64. Since the prisms 54, 64 are known and can be tested (or is provided with the data), $C_p$ is known or can be readily determined.

From these equations, a number of parameters of the test material can be determined. By subtraction of the equations, the influence of $\Sigma T_e$ can be eliminated. For purposes of description, the following definitions are applied: $T_2-T_1=\Delta T_{21}$; $T_1-T_2=\Delta T_{12}$; $T_1-T_3=\Delta T_{13}$; $T_2-T_4=\Delta T_{24}$ Before examining the use of the measured signal parameter for both signal paths, it is worth noting that each of configurations (FIG. 1 or FIG. 2) allows a determination of the flow velocity of the test material through the conduit 12

For example, subtracting $T_1$ (the downstream TOF in FIG. 1) from $T_2$ (the upstream TOF in FIG. 1) provides:

$$\Delta T_{21} = \frac{2X_1 V\sin\alpha}{[C^2 - (V\sin\alpha)^2]} \quad (6a)$$

However, the subtrahend in the denominator is small compared to $c^2$ and can be ignored to provide:

$$\Delta T_{21} = \frac{2X_1 V\sin\alpha}{C^2} \quad (6b)$$

And this is this equation that known transient time flow meters are based on. Undesireably, the measured flow velocity depends on sound velocity C of flowing material.

Consider measurements from both of the unique signal paths for the case where the external components are equal. For the T1 and T3 signal paths, the following expression follows from equations (1) and (2):

$$\frac{1}{\Delta T_{13}} = \frac{C \cdot \cos\alpha}{\Delta d} \quad (7)$$

If all four measured TOF T1, T2, T3 and T4 are employed, then:

$$C = \frac{\Delta d}{\cos\alpha (\sqrt{\Delta T_{13} \cdot \Delta T_{24}})} \quad (8)$$

which can be rewritten with equation (5) as:

$$C = \left(\frac{\Delta d}{(\sqrt{\Delta T_{13} \cdot \Delta T_{24}})}\right) \cdot \sqrt{\frac{2}{2 - 4\left(\frac{(\sin\beta)}{C_p}\right)^2 \cdot \frac{\Delta d^2}{\Delta T_{13} \cdot \Delta T_{24}}}} \quad (8a)$$

This expression provides for directly determining the sound velocity by means of two measured parameters $\Delta T_{13}$ and $\Delta T_{24}$.

Equation (5) fully defines α as a function of C. Therefore, equation (7) and/or (8) establish a means to measure the acoustic velocity of the test material unaffected by the acoustic properties materials outside or external to the test material. Acoustic velocity is generally a function of liquid composition and mixing ratios including parameters such as liquid temperature, salinity and pressure as well as blood protein concentration. Therefore, in situations where only one such liquid property is unknown, equation (7) and/or (8) provide a means for measuring (or determining) the unknown liquid property.

Measurements from both the unique signal paths also provide a means to measure flow unaffected by the acoustic velocity dependence in equation 6b. Equations (1) through (4) yield the expressions:

$$\Delta T_{13} = \frac{X_1 - X_2}{C + V\sin\alpha} \quad (9a)$$

$$\Delta T_{24} = \frac{X_1 - X_2}{C - V\sin\alpha} \quad (9b)$$

By the definitions, $\Delta d=(X_1-X_2)\cos\alpha$. C can be eliminated from equations 9(a) and 9(b) to arrive at the following expression for the flow velocity:

$$V = \frac{\Delta d}{2\sin\alpha\cos\alpha}\left[\frac{1}{\Delta T_{13}} - \frac{1}{\Delta T_{24}}\right] \quad (10)$$

Thus, the sound velocity C and the flow velocity V can be found accurately and independently of the sensor probe materials, the conduit walls, the temperature, and the external signal path.

The determination of the parameters of the test material is independent of deposits on the conduit wall. The deposits can include a build-up of foreign matter in the test material, e.g. wall build-up in bloodlines, human and animal vessels, etc. Since such deposits are often homogeneous for the measuring area, such as along the signal path, the determination of the desired parameters of the test material is independent of such deposits. Alternatively, if the deposits represent a non-uniformity of the local region of the conduit wall, they can be detected by present probe. Generally, for an object that is homogeneous along the signal path, such as the object being reasonably transparent with respect to the measuring signal along the signal path, then the resulting measurements will not be affected by the presence of such object, whether deliberately located in the signal path or unintentionally occurring in the signal path.

Attenuation coefficient δ is another independent intrinsic parameter that can be determined. The attenuation coefficient is determined from measured values of wave attenuation along the signal paths.

Attenuation of a propagating signal (wave) is expressed by:

$$A = A_0 e^{-\delta x} \quad (11)$$

where $A_0$ is the amplitude of the emitted wave and x is a distance.

The attenuation of the measuring signal from the transmitting transducer to a receiving transducer along the signal path is:

$$A = A_0 e^{-\Sigma \delta_e x_e} \cdot e^{-\delta x_1} \quad (12)$$

where $e^{-\Sigma \delta_e x_e}$ corresponds to the loss in amplitude (attenuation) from the external signal path; and $e^{-\delta x_1}$ corresponds to the loss in amplitude (attenuation) from the measuring signal passing along the internal signal path (through the test material).

For the pair of measurements of the received amplitude A1 and A2 taken along the different signal paths (different signal path lengths through the test material), with the difference in length of the internal portions being known, the ratio of measured amplitudes becomes:

$$\frac{A1}{A2} = e^{-\delta(x1-x2)} = e^{-\delta \Delta x} \quad (13)$$

From this ratio, the attenuation coefficient δ is readily determined.

Thus, a single sensor probe 20 using a single frequency (parameter) of a measuring signal (in this case an ultrasonic wave) through 3 pairs of measurements allows three independent parameters of a test material to be determined—sound velocity C, flow velocity V and attenuation coefficient δ.

The calculations can be performed by any of a variety of mechanisms including a controller such as signal processors and computers, including programmed desk or laptop computers, or dedicated computers for processors. Such controllers can be readily programmed to perform the recited calculations, or derivations thereof, to provide determinations of the parameters of the test material. The controller can also perform preliminary signal conditioning such as summing one signal with another signal or portion of another signal.

Since the measurements are obtained with a single sensor probe and can be done practically simultaneously (within the order of a given time of flight of the measuring signal), the correlation of the data will have reduced errors. That is, transient variables such as temperature will have a reduced or negligible effect on the determined parameter of the test material.

Further, such parameters as sound velocity and attenuation coefficient provide for calculation of additional parameters of the test material. For example, if blood is the test material, then blood proteins and/or water content can also be determined, while minimizing the impact of otherwise interfering factors or influences such as temperature, conduit (tubing) material and conduit wall thickness.

Although a transducer 52, 62 is shown at each end of the signal path, it is understood that one of the transducers can be replaced with a reflector. In this construction, the measuring signal sent by the transducer travels to the reflector and is reflected back along the same signal path to be received by the transducer. While such configuration does not provide a measurement of the flow velocity, the remaining parameters (sound velocity C and attenuation coefficient δ) can be provided with enhanced accuracy (sensitivity) as the measuring signal passes through the test material twice.

It is further contemplated that a number of different frequencies, short pulses, or sweeping frequencies can be used to further enhance the present method.

With the dynamic sensor probe 20, the determination of test material parameters is characterized by the serial retrieval of information, in that one set of measurements is made with the sensor probe in the first position (defining a wider channel) and a second set of measurements is made with the sensor probe in the second position (defining a narrowed configuration).

There are numerous advantages to the dynamic sensor probe construction in that the measurement channel 34 has a simple construction and can be applied for a wide range of conduit sizes using a single probe. However, it is understood that an actuator is required for configuring the channel 34 and thus can have limited application for dynamic process measurements such as quickly moving fluids. The actuator can be mechanical such as piezoactuators, gears or racks, hydraulic or pneumatic. The actuator can be operably connected to the controller for selectively being disposed in the first or second position.

Figure 4:
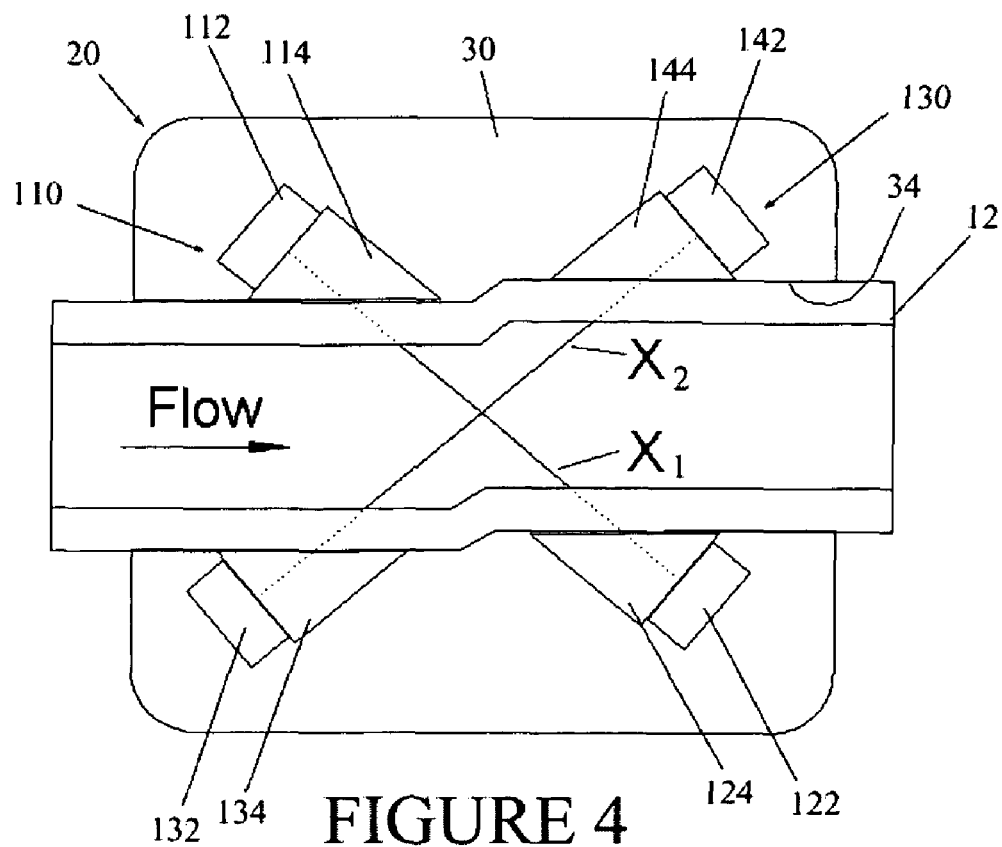
FIG. 4 is a cross-sectional view of an alternative configuration of the static sensor probe.
Figure 5:
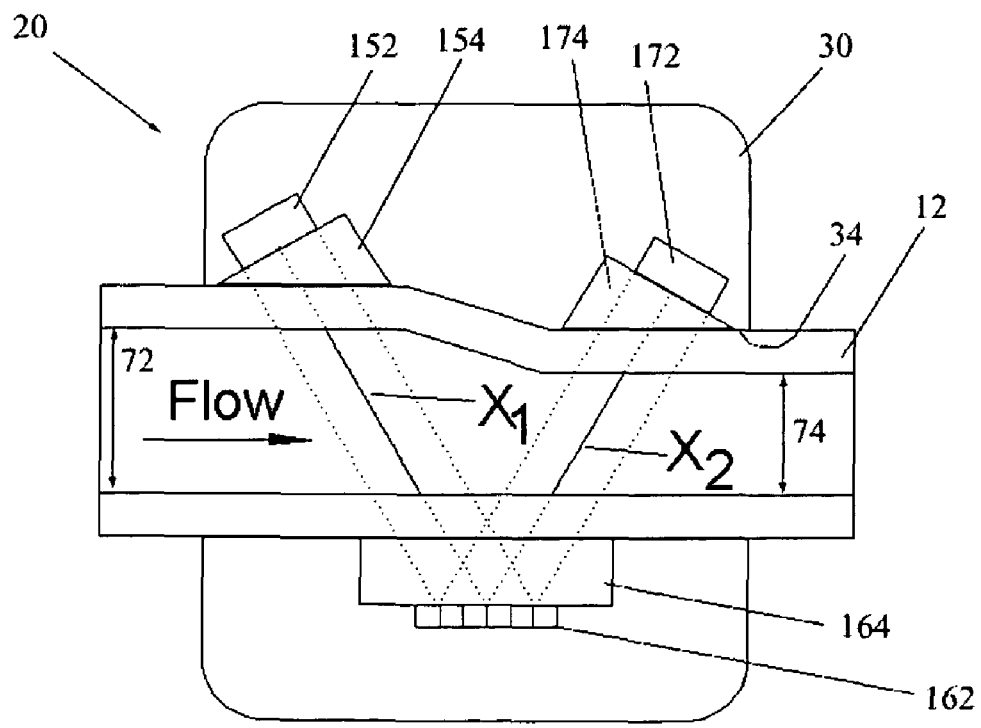
FIG. 5 is a cross-sectional view of a further configuration of the static sensor probe.

Although the measuring signal can be measured with the dynamic sensor probe 20, it is understood the same calculations can be made from a static sensor probe. Representative static sensor probes 20 are shown in FIGS. 3-5.

Generally, the static sensor probe 20 defines a permanent construction of channel 34 to provide two unique permanent internal signal paths. The signal paths are unique in that the internal portion of each path is of a different length. In the static sensor probe configuration, the measuring signals can simultaneously pass along the signal paths, thereby providing parallel information gathering. While the cross-sectional area of the conduit 12 associated with each of the internal signal paths can be different, in a preferred construction the cross-sectional area of the conduit and its shape are constant.

Figure 3:
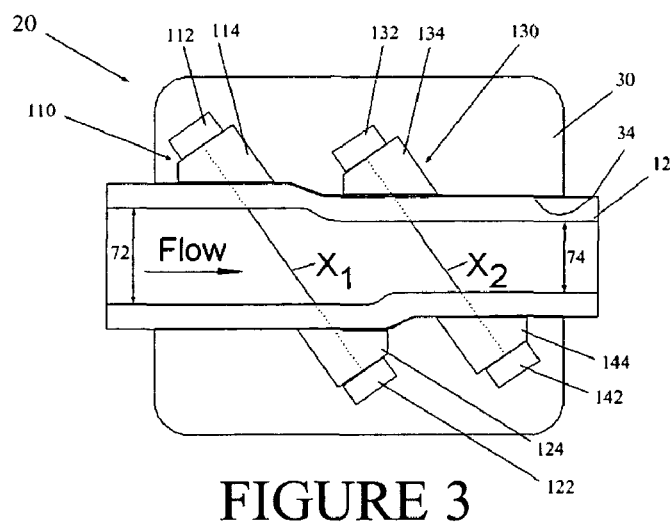
FIG. 3 is a cross-sectional view of a static sensor probe.

Referring to FIG. 3, the conduit 12 within the sensor probe 20 defines a wide section 72 and a narrow section 74, wherein an internal portion $X_1$ of a first signal path extends across the wide section and an internal portion $X_2$ of a second signal path extends across the narrow portion. The external portions of the signal paths are constructed to be identical. As the external portion of both the first signal path and the second signal path are identical (known or calibrated), the previously described equations are applicable to the static sensor probe 20.

Specifically, as shown in FIG. 3, external component of the first signal path includes a first sensor assembly 110 and external component of the second signal path includes a second sensor assembly 130. The first sensor assembly 110 includes an upstream transducer 112, an upstream prism 114, a downstream transducer 122, and a downstream prism 124. Thus, the first signal path includes the first sensor assembly 110 and two thicknesses of the conduit wall.

The second sensor assembly 130 includes an upstream transducer 132, an upstream prism 134, a downstream transducer 142, and a downstream prism 144. Thus, the second signal path includes the second sensor assembly 130 and two thicknesses of the conduit wall.

It is understood various coupling layers or media can be connected to the respective prisms and transducers. Preferably, as in the dynamic sensor probe, the external portions of each of the signal paths are identical.

Knowing the difference in the internal portions of the signal paths, the measuring signal is again considered. The time of flight (TOF) $T_1$ for an acoustic measuring signal passing along the first signal path from the upstream transducer 112 to the downstream transducer 122, as shown in FIG. 3, is:

$$T_1 = \sum T_e + \frac{X_1}{(C + V\sin\alpha)} \quad (14)$$

where $\Sigma T_e$ is the total time of flight of the measuring signal along the external portion of the signal path, C is the intrinsic velocity of sound in the test media, and V is the velocity of the test material flow through the conduit 12.

The time of flight ($T_2$) for an acoustic measuring signal passing along the first signal path from the downstream transducer 122 to the upstream transducer 112, as shown in FIG. 3, is:

$$T_2 = \sum T_e + \frac{X_1}{(C - V\sin\alpha)} \quad (15)$$

The time of flight ($T_3$) for an acoustic measuring signal passing along the second signal path from the upstream transducer 132 to the downstream transducer 142, as shown in FIG. 3, is:

$$T_3 = \sum T_e + \frac{X_2}{(C + V\sin\alpha)} \quad (16)$$

The time of flight ($T_4$) for an acoustic measuring signal passing along the second signal path from the downstream transducer 142 to the upstream transducer 132, as shown in FIG. 3, is:

$$T_4 = \sum T_e + \frac{X_2}{(C - V\sin\alpha)} \quad (17)$$

It is understood that $\Sigma T_e$ can vary substantially, such as in response to temperature changes. However, it is understood other dependencies such as pressure and time can exist.

As previously set forth, the material parameters can be determined from these measured signal parameters.

In a preferred configuration of the static sensor probe 20, both the cross-sectional area of the conduit 12 and the cross-sectional shape of the conduit are maintained at the longitudinal position of the first internal signal path and the different second internal signal path. Referring to FIG. 4, a housing 30 and channel 34 are provided wherein the cross-sectional area and shape of the conduit 12 are maintained in both the first and the second signal paths. A longitudinal dimension of the conduit 12 includes an offset. In this construction, the static sensor probe 20 includes the first transducer assembly 110 and the second transducer assembly 130, wherein the respective signal paths define a generally "X" shape extending along the longitudinal offset of the conduit 12. Thus, the internal portion of the signal path between transducers 112 and 122 is different (shorter) than the internal portion of the signal path between transducers 132 and 142.

An advantage of the static sensor probe 20 configuration of FIG. 4 is that the width of the conduit 12 does not change within the sensor probe; the longitudinal axis of the conduit is merely shifted. However, as in the dynamic sensor probes, the external portion of each signal path is identical or is calibrated prior to measurement of the measuring signal. For all configurations of the sensor probe 20, it is preferable the angles of incidence of both measuring signals (waves) in the respective sensor pairs and the prisms are identical between the sensor assemblies 110, 130.

In the static sensor probe 20, the transmission of the measuring signals can be simultaneous or sequenced in any order. For example, the first measuring signal can be emitted by transducer 112 and received by transducer 122; then, the second measuring signal can be emitted by transducer 132 and received by transducer 142. Alternatively, transducer 112 and transducer 132 can simultaneously emit a corresponding measuring signal that is received and measured at the corresponding transducer.

A further configuration of the static sensor probe 20 is shown in FIG. 5. The housing 30 includes the channel 34 defining the wide section 72 and the narrow section 74. The sensor probe 20 includes an upstream transducer 152, a downstream transducer 172, and an intermediate transducer 162. The upstream transducer 152 cooperates within an upstream prism 154, and the downstream transducer 172 cooperates with a downstream prism 174. In a preferred construction, the upstream transducer 152 and the downstream transducer 172 are disposed along one side of the conduit 12, and the intermediate transducer 162 is disposed on the opposing side of the conduit, longitudinally intermediate the upstream transducer and the downstream transducer. The intermediate transducer 162 can be acoustically coupled with rectangular acoustic block or prism 164. In this configuration, the signal paths generally define a "V" shape.

The first signal path passes from the upstream transducer 152 to the intermediate transducer 162 across the wide section 72, and the second signal path extends from the downstream transducer 172 to the intermediate transducer 162 across the narrow section 74.

As described for the prior constructions, the measuring signal passes along the first and second signal path and is processed to provide a parameter of the test material.

For any construction of the sensor probe 20, it is understood the measuring signal (waves or fields) can be of any physical origin. For purposes of illustration, the measuring signal is described in terms of ultrasonic signals. Further, the measuring signal can be used in combination with any other type of sensor (preferably the non-interfering manner) such as ultrasonic, electromagnetic, magnet, optical, electrical, thermal and chemical. These additional sensors can be integrally located within a housing body frame of the dynamic or static sensor probe.

While it is contemplated the transducers in the static or dynamic sensor probes are disposed on a single plane, thereby permitting ease of insertion and extraction of flexible conduits into and out of the channel, it is understood that a liquid flowing in an open channel or a closed channel having a movable cover can be employed.

In the closed conduit 12 (such as with in-line probes) where insertion of a flexible conduit is possible, the sensor assemblies and corresponding transducers can be disposed on orthogonal planes through the axis of the conduit (FIGS. 6-9). These constructions can measure both real-time flow rate (of a fluid test material) and parameters of the test material.

In these configurations, the sensor probe 20 provides a relatively undisturbed flow through the conduit 12, such that there are no distinct deviations in either the periphery or central axis of the conduit.

Figure 6:
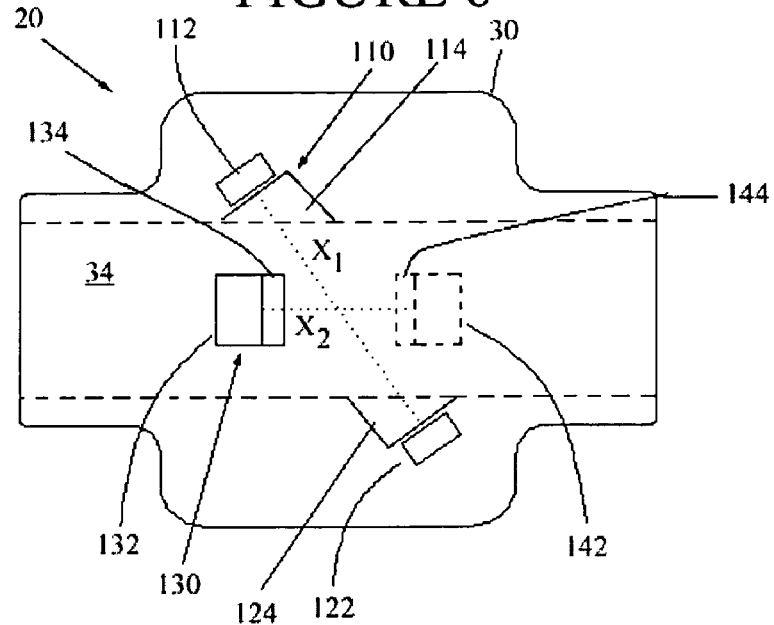
FIG. 6 is a schematic representation of a sensor probe having a pair of sensor assemblies and a rectangular channel.
Figure 7:
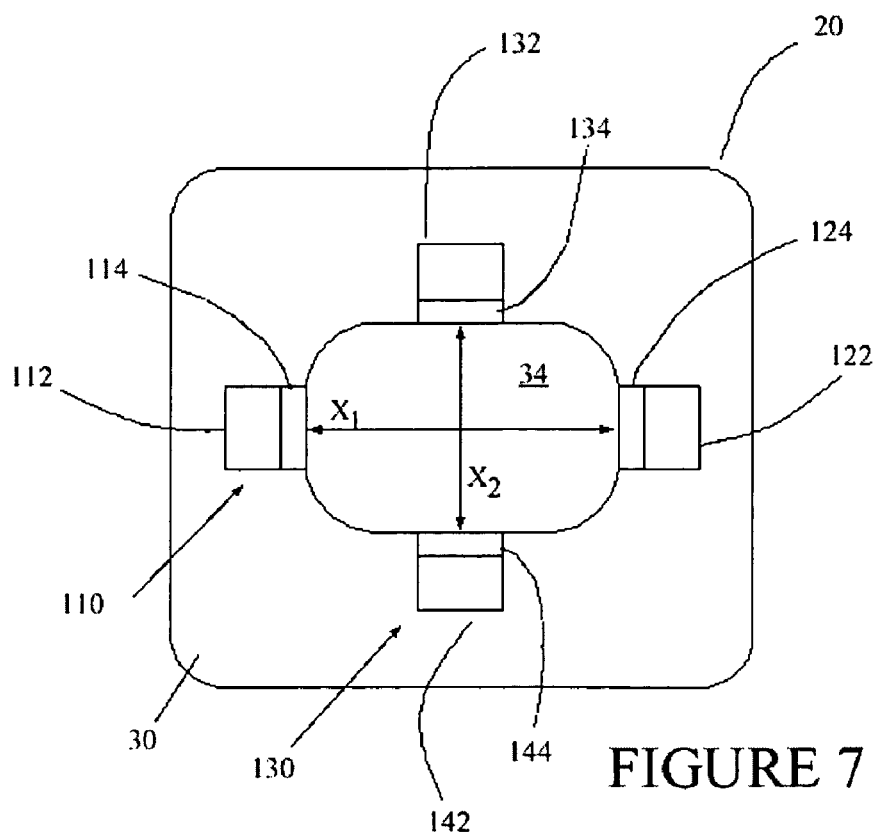
FIG. 7 is a schematic side view of the sensor probe of FIG. 6.

Referring to FIGS. 6-10, the sensor probe 20 provides the housing 30 having the channel 34 with first and second sensor assemblies 110, 130. As shown in FIG. 7, the channel 34 defines a generally rectangular cross section, and the first sensor assembly 110 includes a signal path extending along the longer dimension of the channel and the second sensor assembly 130 includes a signal path extending along the shorter dimension of the channel.

Depending upon the material of the housing 30, the first sensor assembly 110 can include the upstream prism 114 and the downstream prism 124, and the second sensor assembly can include the upstream prism 134 and the downstream prism 144.

In this configuration of the static sensor probe 20, the signal parameters can be measured simultaneously; and the conduit 12 defines a common cross-sectional area for both unique signal paths.

Figure 8:
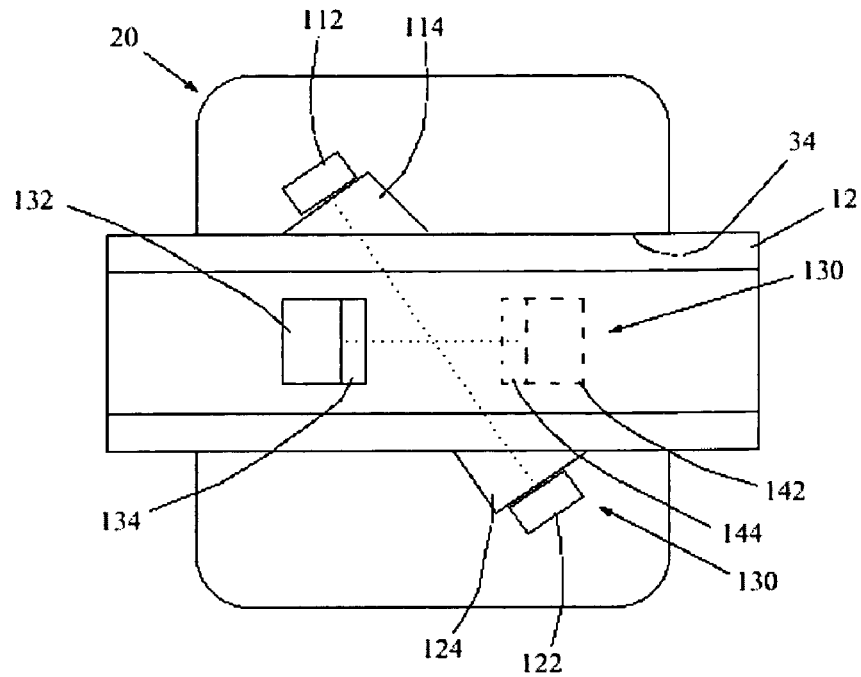
FIG. 8 is a schematic representation of the sensor probe of FIG. 6, including a flexible conduit.
Figure 9:
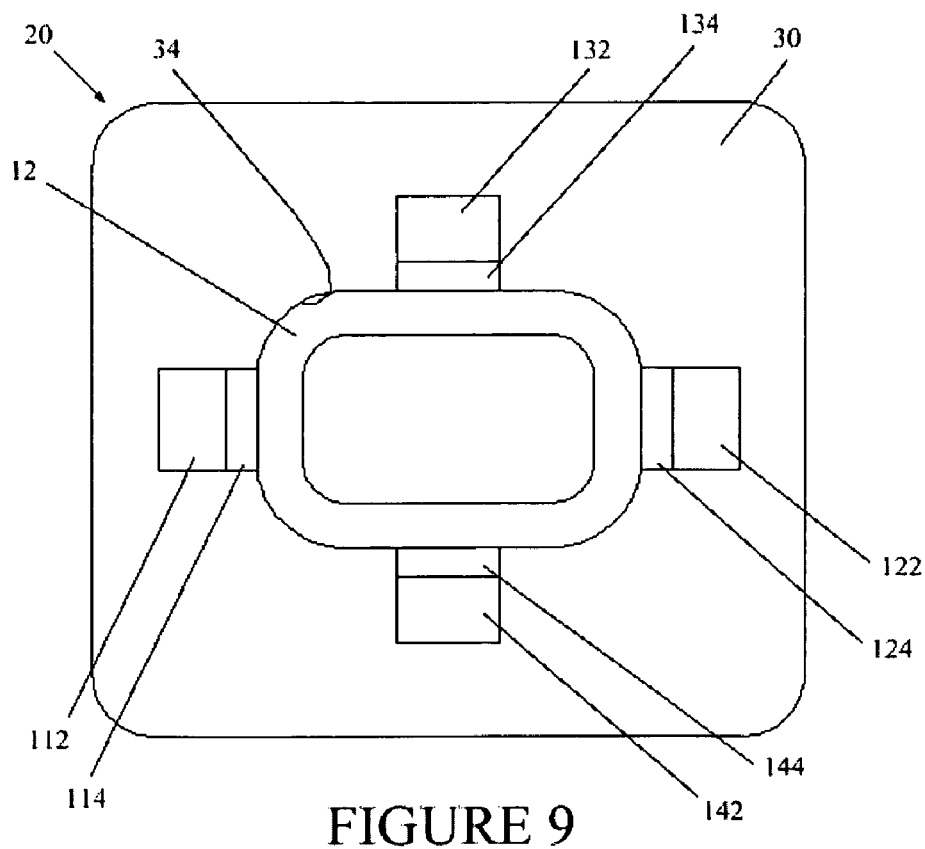
FIG. 9 is a schematic side view of the sensor probe of FIG. 8.
Figure 10:
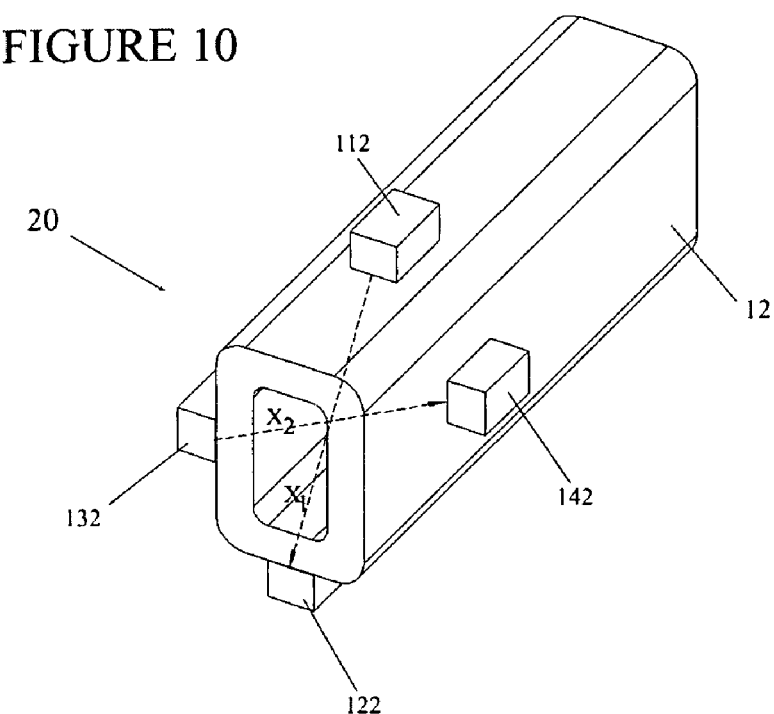
FIG. 10 is a schematic perspective view of the static sensor probe of FIGS. 6-9.

Referring to FIGS. 8 and 9, the in-line ultrasonic sensor probe 20 of FIGS. 6 and 7 is shown with a thin-walled conduit such as a metal conduit. The metal can be any of a variety of materials, such as those used in the medical industry including, but not limited to, stainless steel or titanium.

In FIGS. 6-10, the housing 30 renders the conduit 20 to define a cross section and the sensor assemblies 110, 130 are located such that the first and second unique signal paths exist at a common location in the conduit. The first and second sensor assemblies 110, 130 can include upstream and downstream sensors to allow for determination of flow velocity V.

Figure 11:
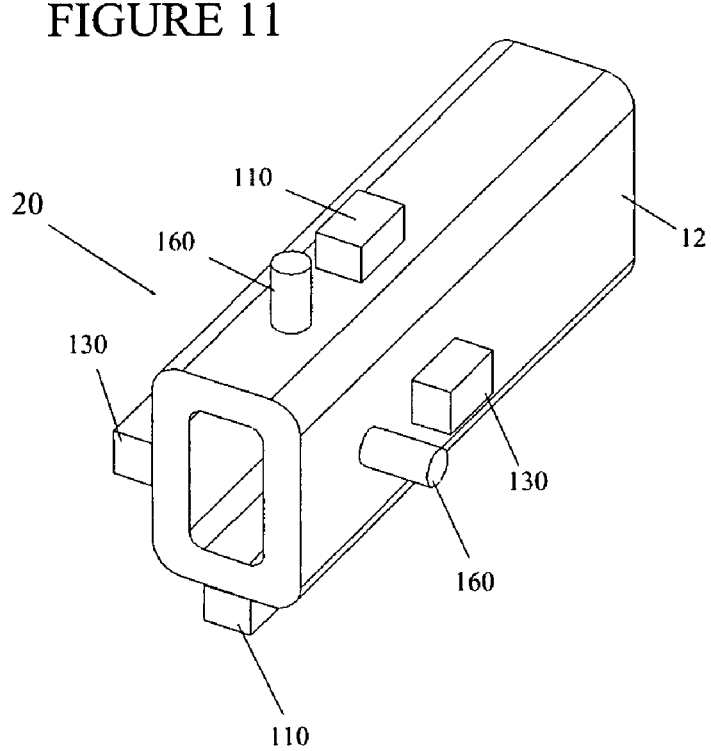
FIG. 11 is a schematic perspective view of a static sensor probe of FIG. 10 employing additional sensors.

As seen in FIG. 11, a schematic representation of an alternative configuration of the static sensor probe is provided wherein additional sensors 160 are employed. The sensor assemblies 110, 130 are constructed such that each signal path includes a component extending along the longitudinal dimension of the conduit 12 that is along the direction of flow of the test material. The measurement of corresponding measuring signals passing along the first and second signal paths in this configuration permits for simultaneous measurement of two parameters such as the sound velocity in the test material (intrinsic parameter) and flow rate of the test material (a parameter of state) in a flexible conduit by means of the sensor probe having four ultrasonic transducers.

Figure 12:
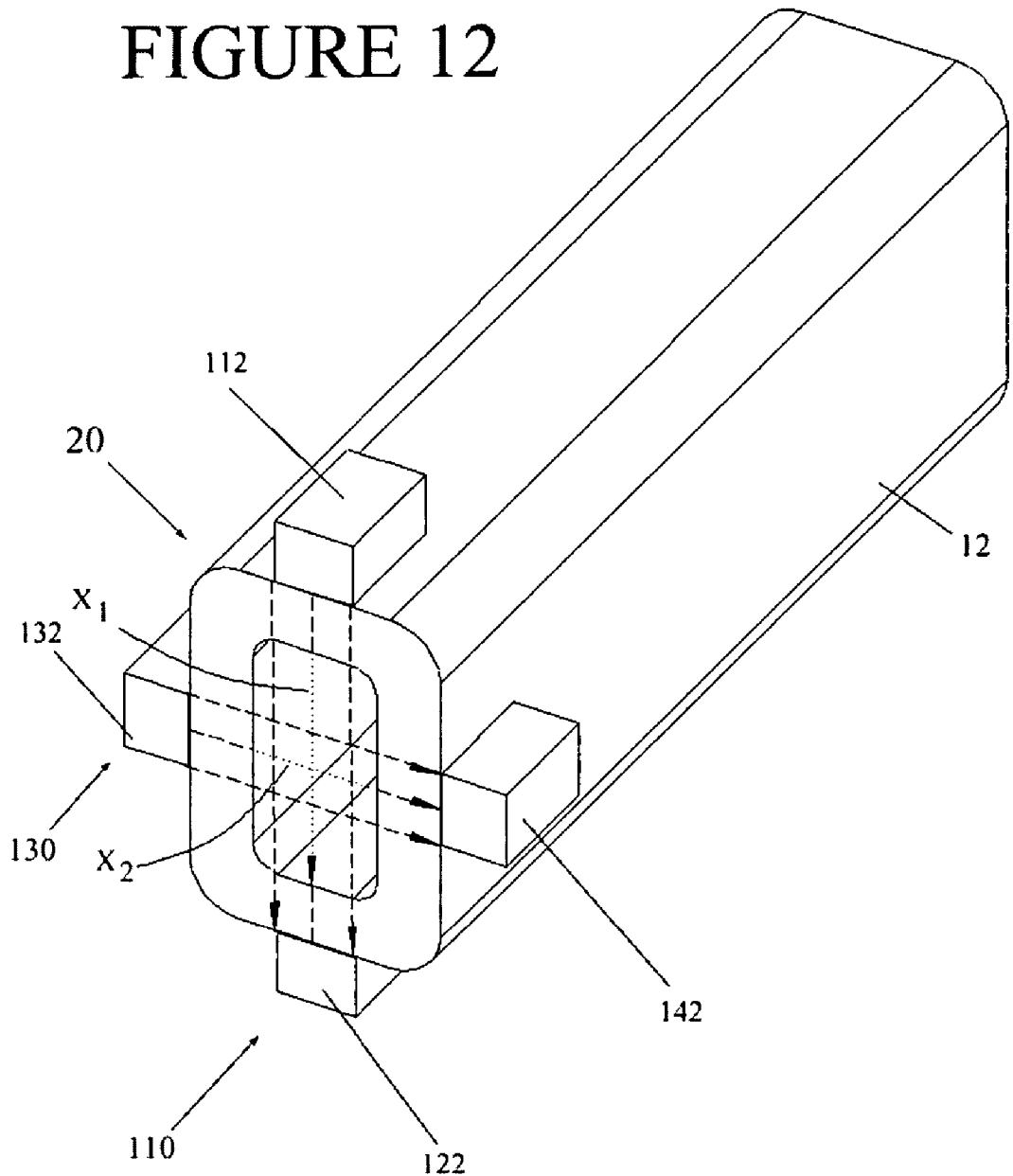
FIG. 12 is a schematic perspective view of a static sensor probe.

Referring to FIG. 12, a configuration of the static sensor probe 20 is shown for use with a flexible conduit 12, such as round polymer tubing. The housing either defines or provides a predetermined cross-sectional configuration of the conduit 12. The sensor probe 20 includes a pair of sensor assemblies 110, 130, each sensor assembly including a sending transducer 112, 132 and a receiving transducer 122, 142. The respective signal paths of the sensor assemblies are shown in dotted lines in the figure, wherein the signal path length for the first sensor assembly is set forth as D1, and the signal path length for the second sensor assembly is set forth as D2.

A time of flight of a signal (such as an ultrasound pulse) for the first and second sensor assembly of FIG. 12 can be written as:

$$T1 = \sum T11 + \sum T12 + \frac{X1}{C} \quad (18, 19)$$

$$T2 = \sum T11 + \sum T12 + \frac{X2}{C}$$

where $\Sigma T11$ is the time delay within the sensor probe, $\Sigma T12$ is the time of flight within the conduit wall, X1 is the length of the first signal path through the test material, X2 is the length of the second signal path through the test material and C is the velocity of sound in the test material.

For the sensor probe shown in FIG. 12, assuming the conduit wall thickness is constant in each signal path, then the following relationship holds:

$$X1-X2=D1-D2=\text{constant} \quad (20)$$

then, subtracting T2 from T1 provides:

$$T1 - T2 = \frac{(X1 - X2)}{C} \quad (21)$$

Solving for C yields:

$$C = \frac{(X1 - X2)}{(T1 - T2)} \quad (22)$$

Therefore, the velocity of sound in the test material can be determined independent of the conduit 12, the conduit wall thickness, the conduit wall material and temperature. The elimination of these factors increases the accuracy of the determined velocity of sound in the test material.

One configuration of the sensor probe 20 thus provides for passing the measuring signal along the first signal path and obtaining a first value of the measuring signal, then changing a spacing between the walls and passing the measuring signal along the second signal path and obtaining a second value of the measuring signal.

As the influence of the external portion of the signal path, such as the housing 30 and conduit parameters as well as transient influences such as temperature, can be effectively eliminated from the calculation of the desired parameter of the test material, the accuracy of the determined material parameters is increased. The probe elements surrounding the signal paths provide equal thermal conductivity in regard of ambient temperature. It is desirable to have such thermal conductivity as low as possible. In instances where ambient effects on the external portion of the signal path may influence the value of the measured parameter, care must be taken in the sensor design to ensure that such influence is the same for each signal path. For example, where the ambient temperature can alter the ultrasound transit time within the transducer prisms and the conduit walls, or where stray ambient light can alter readings in optical sensors, the sensor probe is preferably constructed to ensure that such effects are at least substantially equal for each signal path and minimized within each signal path.

Further, the simultaneous measurement of several parameters of the test material from a single type of measuring signal and the resulting matrix further allows increased reliability. That is, the simultaneous usage of the same signal paths of several measuring signals provides measurements which can be joined and data processed as a matrix or vector, further enhancing the usefulness of the measurements.

It is contemplated the measuring signals can have different frequencies; and thus, for example, by measuring signal attenuation, followed by ratio metric data processing, the reliability of the determined parameters is increased. The substantially simultaneous measuring and processing can provide additional information as well as increased accuracy of the results due to mutual correlation of the measurements. Employing measuring signals of different frequencies, and through the use of measuring signal attenuation followed by ratio metric or related data processing, substantial increases in measurement accuracy can be provided.

In a further embodiment, it is contemplated that the housing 30 such as in the static sensor probe defining two fixed unique signal paths, can be incorporated within a dynamic housing to move the respective sensor assemblies to a second position, thereby defining a third and a fourth unique signal path. The resulting additional data can be used for increasing accuracy of the determined parameters.

A variety of parameters can be determined by the present invention including intrinsic parameters of the test material as well as variations in the intrinsic parameters as a function of time, pressure or temperature. For example, the viscosity, acoustic velocity, coefficient of attenuation and density of the test material can be determined. Further, combined processing of the simultaneously measured signal parameters allows getting more reliable information due to potential correlation between the test material parameters. This is especially important when there is interest in determination of intrinsic parameters of the test material as a function of time, and/or other direct or indirect factors including but not limited to temperature, pressure, admixtures, dilution, filtration and aging. The obtained combination of correlated parameters can be used either as an end product or for generating diagnostic signals and/or assessments of the progress or efficacy of processes such as hemodialysis, purification of liquids, and filtrations.

Figure 13:
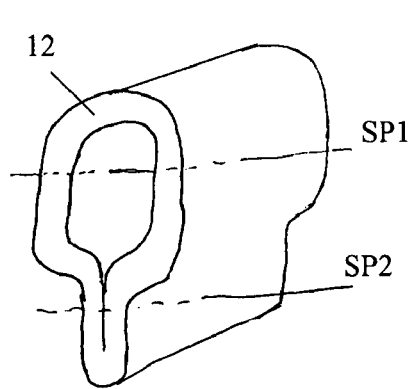
FIG. 13 is a cross sectional perspective view of a further configuration of the static sensor probe showing a signal path external to the test material.
Figure 14:
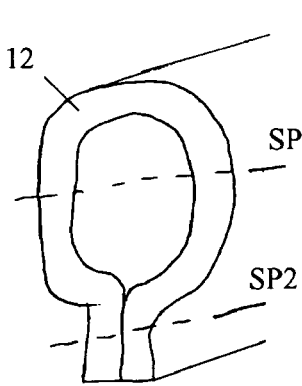
FIG. 14 is a cross sectional perspective view of a further configuration of the static sensor probe showing a signal path external to the test material.
Figure 15:
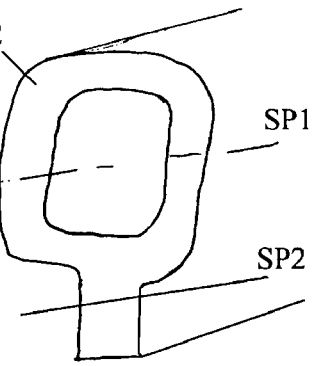
FIG. 15 is a cross sectional perspective view of a further configuration of the static sensor probe showing a signal path external to the test material.

In a further configuration, the sensor probe 20 can be configured to provide first and second signal paths SP1, SP2 having differing internal and external components. Specifically, referring to FIGS. 13-15, the internal component of one of the signal paths SP2 is eliminated (a zero value). The external components of the signal paths can be any of a variety of constructions to provide equal impact on the measuring signal. Thus, for an internal component of 0 for the second signal path, equation 22 becomes:

$$C = \frac{(X1)}{(T1-T2)} \quad (23)$$

In addition, although preferable that the external component of each signal path has identical impact on the measuring signal, it is understood a variance can exist between the external components of the first and second signal paths. The variance between the external components can be within an acceptable limit for desired accuracy, or can be accommodated by a correction factor for the sensor probe 20.

It is also understood the test material can be any static or dynamic; that is, the test material can be flowing or stationary.

It is contemplated that a temperature sensor such as a thermocouple or thermistor can be used in connection with the sensor probe 20. The temperature sensor can be located to be thermally coupled to the test material. Preferably, the thermal coupling of the temperature sensor to the test material is sufficient to provide an accurate indication or measurement of the relevant temperature.

Further, if fluid temperature inside the measuring volume (along the signal paths) is to be maintained within certain limits, or changed in accordance to a desired function, a temperature controller (heater/coolers) can be employed to regulate the temperature. For example, Peltier cooling/heating elements can be employed to control the temperature of the test material. The temperature regulators can be connected to the controller for coordinated operation with the sensor assemblies.

Although a varying temperature or temperature instability has been an adverse factor in prior devices, the ability of the present sensor probe 20, such as with the ultrasonic measuring signal, to react to temperature changes in the test material, substantially instantaneously and without wall or conduit influence can be advantageously used in monitoring the test material.

It is also contemplated that the measuring signals can be created or excited on a signal path within the test material. For example, but not limited fluorescence, Doppler, Hall, Faraday or other effects can be measured along two different paths and processed as described.

Satisfactory material for the channel/conduit 12 has been found to include a variety of polymers and plastics including Pebax, silicone rubber, PVC, Ultem, polystyrene and also thin-walled metal.

Similarly, the sensor assemblies can be of various types, such as those sold by Transonic Systems, Inc, and disclosed in U.S. Pat. No. 6,098,466 issued Aug. 8, 2000 in the name of the present inventor.

While the invention has been described in conjunction with specific embodiments thereof, it is evident that many alternatives, modifications, and variations will be apparent to those skilled in the art in light of the foregoing description. Accordingly, the present invention is intended to embrace all such alternatives, modifications, and variations as fall within the spirit and broad scope of the appended claims.

The invention claimed is:

1. A method of passing a measuring signal through a test material located between at least two spaced walls, the method comprising:
   (a) at least one of emitting and receiving the measuring signal from at least one transducer;
   (b) passing the measuring signal associated with the at least one transducer along a first signal path and a second signal path through the test material and the at least two spaced walls, the first and the second signal paths having equal or known external components and the first and the second signal paths having different straight lengths within the test material; and
   (c) measuring at least one signal parameter of the measuring signal passed along the first signal path and the second signal path, wherein the at least one signal parameter of the measuring signal is changed by the passing of the measuring signal through the test material.

2. The method of claim 1, wherein the at least one signal parameter includes at least one of a time of flight, phase, frequency, intensity, amplitude, and attenuation of the measuring signal.

3. The method of claim 1, further comprising determining at least one of an intrinsic characteristic or a parameter of condition of the test material.

4. The method of claim 1, further comprising performing a preliminary signal conditioning on the measuring signal passing along at least one of the first signal path and the second signal path.

5. A method of passing a measuring signal through a test material located between at least two spaced walls, the method comprising:
   (a) at least one of emitting and receiving the measuring signal from at least one transducer; and
   (b) passing the measuring signal associated with the at least one transducer along a first signal path and a second signal path through the test material and the at least two walls, the first and the second signal paths having equal external components and the first and the second signal paths having different straight lengths within the test material, wherein passing the measuring signal along the first signal path and the second signal path includes passing the measuring signal along different portions of a given section of the test material.

6. A method of passing a measuring signal through a test material located between at least two spaced walls, the method comprising:
(a) at least one of emitting and receiving the measuring signal from at least one transducer;
(b) passing the measuring signal associated with the at least one transducer along a first and a second signal path, the first and second signal paths having different internal lengths within the test material and substantially equal path lengths outside the test material, the path lengths outside the test material including the at least two spaced walls, and
(c) simultaneously or substantially simultaneously measuring the measuring signal along the first signal path and the second signal path.

7. A method of determining a characteristic of a test material located between at least two spaced walls, the method comprising:
(a) at least one of emitting and receiving the measuring signal from at least one transducer;
(b) passing the measuring signal associated with the at least one transducer along a first and a second signal path, the first signal path having a first external component and a first internal component, the first external component including the at least two spaced walls, the second signal path including a second external component and a second internal component, the second external component including the at least two spaced walls, the first external component and the second external component being substantially equal or known, and the first internal component having a different length than the second internal component within the test, and
(c) determining the characteristic of the test material corresponding to a simultaneously measured signal parameter of the measuring signal passed along the first and second signal paths.

8. A method of determining a characteristic of a test material at least partially bounded by spaced walls, the method comprising:
(a) measuring at least one signal parameter of a first signal along a first signal path, the first signal path having a first internal length within the test material, the first signal path extending through the spaced walls and the test material and terminating at a first sensor separated from the test material by at least one of the spaced walls;
(b) measuring the at least one signal parameter of a second signal along a second signal path, the second signal path having a second internal length within the test material, the second signal path extending through the spaced walls and the test material and terminating at a second sensor separated from the test material by at least one of the spaced walls; and
(c) evaluating a difference between the at least one measured signal parameter of the first and second signals attributable at least in part to the difference between the first and second internal lengths traveled by the first and second signals within the test material for determining at least one characteristic of the test material.

9. The method of claim 8, wherein measuring at least one signal parameter includes measuring one of a time of flight, frequency, amplitude, phase or attenuation of the first signal and the second signal.

10. The method of claim 8, further comprising providing the first signal path with a first external segment external to the test material and the second signal path with a second external segment external to the test material, the first and the second external segments being equal with respect to the measured signal parameter.

11. The method of claim 8, wherein determining at least one characteristic includes determining one of a test material characteristic and a flow characteristic.

12. The method of claim 8, wherein measuring the at least one signal parameter along the first signal path and the second signal path are simultaneous or substantially simultaneous.

13. The method of claim 8, wherein the first internal length and the second internal length are straight.

14. A method of determining at least one characteristic of a test sample located between spaced walls, the method comprising:
(a) positioning at least one transducer outside the test sample for measuring a signal parameter of first and second signals having first and second signal paths with different internal lengths within the test sample and substantially equal path lengths outside the test sample, the path lengths outside the test sample including the spaced walls; and
(b) determining the at least one characteristic of the test sample based on differences in the measured signal parameter between the first and second signals associated with the different internal lengths of the first and second signal paths within the test sample.

15. The method of claim 14, further comprising employing at least one of a time of flight, amplitude, attenuation, frequency, voltage, current, impedance, conductance, transmissivity, opacity, or phase as the signal parameter.

16. The method of claim 14, further comprising employing straight internal lengths.

17. The method of claim 16, further comprising forming the first internal component and the second internal component to be straight.

18. A method of determining a characteristic of a test material located between two spaced walls, the method comprising:
(a) providing a first signal path length having a first internal component within the test material and a first external component, the first external component including both walls;
(b) providing a second signal path having a second internal component within the test material and a second external component, the second external component including both walls, the first and the second internal components being different length, and the first and second external components being equal length;
(c) conveying a first testing signal along the first signal path and a second testing signal along the second signal path, the first and second testing signals having a measuring parameter that undergo a relative change in accordance with a difference between the first and second signal paths;
(d) measuring the parameter of the first testing signal along the first signal path and the parameter of the second testing signal along the second signal path; and
(e) determining at least one material characteristic of the test material based on the measured parameter of the first and second testing signals.

19. A method of determining a characteristic of a test material, comprising:
(a) propagating a pair of signals along a pair of signal paths, each signal path passing through spaced walls, the test material being located between the spaced walls;

(b) monitoring a relative transformation of the pair of signals associated with path length differences through the test material; and (c) determining the characteristic of the test material based on the monitored relative transformation of the pair of signals.

20. The method of claim 19, further comprising determining a different second characteristic of the test material corresponding to a second pair of measurements of the pair of signals passed along the pair of signal paths.

21. The method of claim 20, further comprising simultaneously obtaining the first pair of measurements and the second pair of measurements.

22. The method of claim 19, further comprising determining a different second characteristic of the test material corresponding to a second pair of measurements of a second pair of signals passed along the pair of signal paths.

23. The method of claim 22, further comprising simultaneously obtaining the first pair of measurements and the second pair of measurements.

24. A method of determining a characteristic of a test material located between two spaced walls, the method comprising:

(a) providing a first signal path and a second signal path through the test material and both walls, the first and the second signal paths having equal external components and different straight lengths within the test material;

(b) positioning at least one transducer outside of the spaced walls for measuring a signal parameter of first and second signals propagating along the first and second signal paths; and (c) determining at least one test material characteristic corresponding to differences in the measured signal parameter of the first and second signals.

25. The method of claim 24, further comprising determining a second test material characteristic corresponding to a second measured signal parameter of the first and second signals.

26. The method of claim 24, further comprising determining a second test material characteristic corresponding to a simultaneously measured second signal parameter.

27. A method of determining the property of a test sample located between spaced-apart walls, the method comprising:

(a) at least one of emitting and receiving a measuring signal from at least one transducer located outside the spaced-apart walls;

(b) measuring at least one signal parameter of the measuring signal associated with the at least one transducer along first and second signal paths with different internal lengths within the test sample and substantially equal or known path lengths outside the test sample, the path lengths outside the test sample including the spaced-apart walls; and (c) determining at least one characteristic of the test material corresponding to the measured signal parameter.

28. A sensor probe for measuring a test material between two spaced walls, the sensor probe comprising:

(a) a first sensor assembly having a first signal path with a first external component and a first internal component, the first external component including both walls; and (b) a second sensor assembly having a different second signal path, the second signal path including a second external component and a second internal component, the second external component including both walls, (c) the first external component being substantially equal to the second external component with respect to a measured signal parameter, and the first straight length internal component being different than the second straight length internal component with respect to the measured signal parameter.

29. The sensor probe of claim 28, further comprising a controller connected to the first sensor assembly and the second sensor assembly to determine the characteristic of the test material in response to a parameter of a measuring signal along a first signal path and a second signal path.

30. A sensor probe for measuring a test material in a test volume, the sensor probe comprising:

(a) a sensor housing at least partially defining the test volume;

(b) a first sensor assembly connected to the sensor housing to define a first signal path having a first internal component extending through the test volume and a first external component, the first external component including a pair of spaced walls; and (c) a second sensor assembly connected to the sensor housing to define a different second signal path having a second internal component extending through the test material and a second external component, the second external component including a pair of spaced walls, (d) the first internal component being different than the second internal component.

31. The sensor probe of claim 30, wherein the first external component is substantially equal to the second external component with respect to a signal parameter measured by the first sensor assembly and the second sensor assembly.

32. The sensor probe of claim 30, wherein the first internal component and the second internal component are straight.

33. The sensor probe of claim 30, further comprising a controller connected to the first sensor assembly and the second sensor assembly to determine a difference in the parameter measured by the first sensor assembly and the second sensor assembly.

34. A method for determining a characteristic of a test material, comprising:

(a) locating at least one transducer in a position for at least one of emitting and receiving a measuring signal that passes through the test material;

(b) measuring a first value of a signal parameter of the measuring signal along a first path passing through the test material and a pair of spaced walls, and a second value of the signal parameter of the measuring signal along a different second path passing through the test material and spaced walls; and (c) determining at least one characteristic of the test material corresponding to the first and second measured values of the signal parameter.

35. The method of claim 34, further comprising simultaneously measuring the first value and the second value.

36. The method of claim 34, further comprising substantially simultaneously measuring the first value and the second value.

37. The method of claim 34, further comprising measuring a first value of a second signal parameter along the first path and a second value of the second signal parameter along the second path.

38. The method of claim 37, further comprising determining at least two characteristics of the test material.

39. The method of claim 34, further comprising forming the first path and the second path to be straight.

\* \* \* \* \*